US00PP26056P3

(12) United States Plant Patent
Zaiger et al.

(10) Patent No.: US PP26,056 P3
(45) Date of Patent: Nov. 10, 2015

(54) NECTARINE TREE NAMED 'HONEYLICIOUS'

(50) Latin Name: *Prunus persica var. nucipersica*
Varietal Denomination: Honeylicious

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 88 days.

(21) Appl. No.: 13/999,621

(22) Filed: Mar. 14, 2014

(65) Prior Publication Data

US 2015/0264848 P1 Sep. 17, 2015

(51) Int. Cl.
*A01H 5/00* (2006.01)

(52) U.S. Cl.
USPC ..... Plt./190

(58) Field of Classification Search
USPC ..... Plt./190
See application file for complete search history.

*Primary Examiner* — Annette Para

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit having a high degree of attractive red skin color.
4. Fruit with a mild, sweet, low acid flavor and excellent eating quality.
5. Fruit with firm, yellow flesh with good handling and shipping quality.

1 Drawing Sheet

Botanical designation: *Prunus persica var. nucipersica.*
Variety denomination: 'Honeylicious'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

2. Prior Varieties

Among the existing varieties of nectarine trees, which are known to us, and mentioned herein, 'Honey Royale' Nectarine (U.S. Plant Pat. No. 12,008), 'Honey Gem' Nectarine (U.S. Plant Pat. No. 21,836), 'Honey Lite' Nectarine (U.S. Plant Pat. No. 18,400) and our non-patented proprietary nectarine seedling selections '228LP484' and '52LD434'.

STATEMENT REGARDING FEDERALLY SPONSORED RESEARCH AND DEVELOPMENT

Not applicable.

ORIGIN OF THE VARIETY

The new and distinct nectarine tree (*Prunus persica var. nucipersica*) was originated by us in our experimental orchard from seed of a first generation cross between the non-patented proprietary nectarine seedling '228LP484' and 'Honey Gem' Nectarine (U.S. Plant Pat. No. 21,836). The non-patented nectarine seed parent (228LP484) originated from a cross between our non-patented proprietary nectarine seedling '52LD434' and 'Honey Royale' Nectarine (U.S. Plant Pat. No. 12,008). We planted and grew a large number of these first generation seedlings on their own root system and under close and careful observation we recognized the desirable tree and fruit characteristics of the preent nectarine seedling and selected it in 2007 for additional asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree is of large size, vigorous, upright growth and a productive and regular bearer of large size, yellow flesh, clingstone fruit. The fruit is further characterized by having a mild, sweet, low acid flavor with excellent eating quality. In comparison to its seed parent '228LP484' nectarine (non-patented) the fruit of the new variety is larger in size. In comparison to its pollen parent 'Honey Gem' Nectarine (U.S. Plant Pat. No. 21,836) the fruit of the new variety ripens approximately 24 days earlier. In comparison to the commercial variety 'Honey Lite' Nectarine (U.S. Plant Pat. No. 18,400) the fruit of the new variety is larger in size and is approximately 39 days later in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 6 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, growth of 1.5 meters in height the first growing season. Varies with soil type, fertility and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, adequate fruit set 4 consecutive years. No alternate bearing observed.

*Fertility*.—Self fertile.

*Density*.—Medium dense, usually pruned to vase shape by removing center branches and foliage to allow more sunlight to center of the tree to enhance fruit color and health of fruit wood.

*Hardiness*.—Hardy in all stone fruit growing areas of California. Tree grown in USDA Hardiness Zone 9. Winter chilling requirement approximately 1000 hours at or below 45° F.

Trunk:

*Size*.—Medium. Average circumference 50.8 cm at 20.3 cm above ground on a 6 year old tree.

*Stocky*.—Medium stocky.

*Texture*.—Medium shaggy, roughness increases with age.

*Color*.—Varies from 2.5Y 6/2 to 5Y 5/2.

Branches:

*Size*.—Medium. Average circumference 15.0 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 31 in a 25.8 square cm area. Average length 2.7 mm. Average width 1.6 mm. Color varies from 10YR 5/8 to 10YR 5/10.

*Color*.—New growth varies from 2.5GY 6/6 to 5GY 6/6. Old growth varies from 7.5YR 2/4 to 10YR 3/2, varies with age of growth.

Leaves:

*Size*.—Medium. Average length 102.9 mm. Average width 34.4 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surface glabrous.

*Petiole*.—Average length 9.4 mm. Average width 1.5 mm. Longitudinally grooved. Surface glabrous. Color varies from 5GY 6/10 to 5GY 4/8.

*Glands*.—Type — reniform. Size — small to medium. Average length 1.0 mm. Average diameter 0.7 mm. Number varies from 3 to 7, average number 5. Located primarily on the base of the leaf blade and upper portion of petiole. Color varies from 5YR 3/4 to 2.5GY 5/6.

*Stipules*.—Average length 9.0 mm. Margin — pectinate. Color varies from 2.5GY 6/8 to 5GY 6/8.

*Color*.—Upper surface varies from 5GY 3/4 to 7.5GY 3/4. Lower surface varies from 5GY 4/4 to 7.5GY 4/4. Midvein color varies from 2.5GY 7/4 to 5GY 7/4.

Flower buds:

*Size*.—Large. Average length 17.6 mm. Average diameter 11.1 mm.

*Hardiness*.—Hardy with respect to California winters.

*Form*.—Plump, conical, becoming elongated before opening.

*Pedicel*.—Size — small. Average length 2.6 mm. Average width 1.5 mm. Color varies from 2.5GY 6/8 to 5GY 6/8. Surface — glabrous.

*Color*.—Varies from 5RP 7/10 to 7.5RP 7/8.

Flowers:

*Blooming period*.—Date of First Bloom Mar. 4, 2013. Date of Petal Fall Mar. 14, 2013, varies slightly with climatic conditions.

*Size*.—Large. Average height 21.9 mm. Average diameter 45.5 mm.

*Petals*.—Number — normally 5, alternately arranged to sepals. Average length 21.8 mm. Average width 18.9 mm. Form — orbicular. Arrangement — overlapping. Margin — sinuate. Color varies from 5RP 8/4 to 7.5RP 7/4, fades with age of flower. Both upper and lower surfaces glabrous.

*Sepals*.—Number — normally 5, alternately arranged to petals. Size — large. Average length 6.7 mm. Average width 5.4 mm. Shape — ovate. Margin — entire. Surface — upper surface glabrous. Lower surface pubescent. Color — upper surface varies from 5GY 5/6 to 7.5R 3/4. Lower surface varies from 5R 2/4 to 7.5R 2/4.

*Stamens*.—Average number per flower 41. Average filament length 16.1 mm. Filament color N 9.5/(white) to 5RP 8/6 as flower ages. Anther color varies from 7.5R 3/10 to 5Y 8/8.

*Pollen*.—Self fertile. Color varies from 2.5Y 7/10 to 5Y 7/10.

*Pistil*.—Normally one. Surface — glabrous. Average length 18.5 mm. Position of stigma approximately 1.4 mm below anthers. Color varies from 10Y 8.5/6 to 10Y 8/6.

*Fragrance*.—Moderate aroma.

*Color*.—Varies from 5RP 8/4 to 5RP 7/6.

*Number flowers per flower bud*.—Average number 1.

*Pedicel*.—Average length 4.1 mm. Average width 1.5 mm. Surface — glabrous. Color 2.5GY 6/8.

Fruit:

*Maturity when described*.—Firm ripe.

*Date of first picking*.—Jul. 9, 2013.

*Date of last picking*.—Jul. 19, 2013, varies slightly with climatic conditions.

*Size*.—Large. Average diameter axially 70.0 mm. Average transversely in suture plane 73.8 mm. Average weight 224.4 grams, varies slightly with fertility of the soil, amount of thinning and climatic conditions.

*Form*.—Globose.

*Suture*.—Some fruit with slight suture, extends from base to apex.

*Ventral surface*.—Smooth to slightly lipped.

*Apex*.—Rounded to slight tip on some fruit.

*Base*.—Flat to slightly rounded.

*Stem cavity*.—Rounded to slightly elongated in suture plane. Average depth 6.9 mm. Average diameter 6.2 mm.

Stem:

*Size*.—Small. Average length 8.3 mm. Average diameter 3.0 mm.

*Color*.—Varies from 10Y 6/8 to 7.5YR 4/2.

Flesh:

*Ripens*.—Evenly.

*Texture*.—Firm, meaty.

*Fibers*.—Few, small, tender.

*Firmness*.—Good, comparable to other commercial varieties.

*Aroma*.—Slight.

*Amydgalin*.—Undetected.

*Eating quality*.—Excellent.

*Flavor*.—Excellent, good balance between acid and sugar.

*Juice*.—Heavy amount, enhances flavor.

*Brix*.—Average Brix 12.9°, varies slightly with amount of fruit per tree and climatic conditions.

*Pit cavity*.—Average length 37.8 mm. Average width 27.6 mm. Average depth 13.0 mm. Color varies from 5R 4/8 to 5R 4/10.

*Color*.—Varies from 5Y 8/8 to 5Y 8/10 with 7.5R 4/12 on flesh around pit.

Skin:

*Thickness*.—Medium.

*Surface*.—Smooth.

*Pubescence*.—Wanting.

*Tendency to crack*.—None.

*Color*.—Ground color varies from 5Y 8/6 to 5Y 8/8. Overspread with 7.5R 3/8 to 7.5R 4/12.

*Tenacity*.—Tenacious to flesh.

*Astringency*.—Undetected.

Stone:

*Type*.—Clingstone.

*Size*.—Large. Average length 36.8 mm. Average width 26.6 mm. Average thickness 23.9 mm.

*Form*.—Ovoid.

*Base*.—Flat.

*Apex*.—Pointed. Average length 1.2 mm.

*Surface*.—Pitted throughout, pits vary from round to elongated.

*Sides*.—Unequal, one side extending further from suture plane.

*Ridges*.—Relatively smooth, narrow ridges extending from base toward apex.

*Tendency to split*.—None.

*Color*.—Varies from 5R 3/1 to 5YR 5/8 when dry.

Kernel:

*Size*.—Large. Average length 16.1 mm. Average width 12.5 mm. Average depth 7.5 mm.

*Form*.—Ovoid.

*Viability*.—Viable, complete embryo development.

*Skin*.—Color varies from 2.5Y 8/8 to 2.5Y 8.5/8.

Use: Dessert.

*Market*.—Local and long distance.

Keeping quality: Good, held firm in cold storage at 38° to 42° for three weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

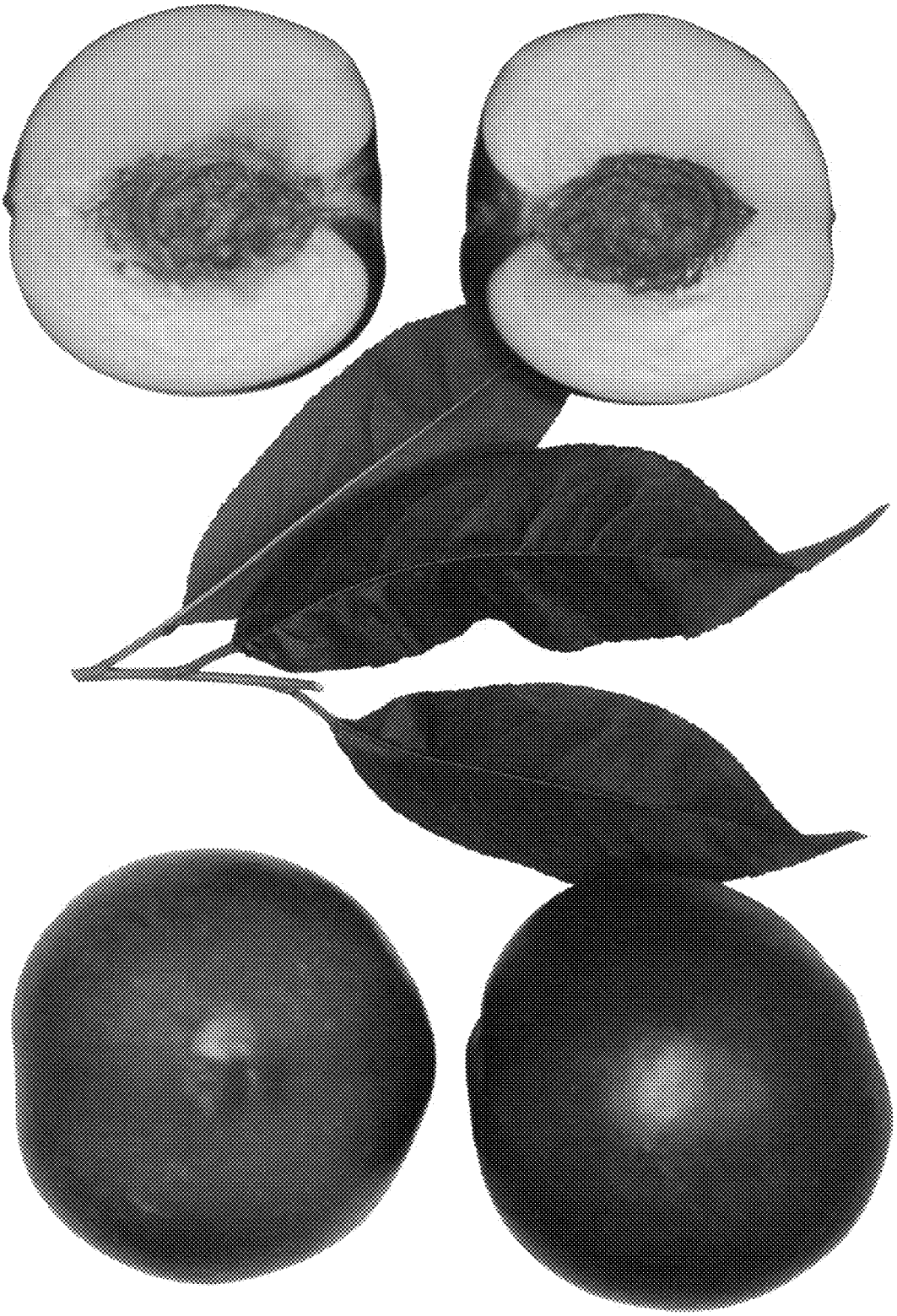

* * * * *